United States Patent
Tuma et al.

(10) Patent No.: US 8,382,759 B2
(45) Date of Patent: Feb. 26, 2013

(54) INTRAMEDULLARY PIN TRACKING

(75) Inventors: Gregor Tuma, Munich (DE); Christian Wende, Puchheim (DE)

(73) Assignee: Brainlab AG, Feldkirchen (DE)

( * ) Notice: Subject to any disclaimer, the term of this patent is extended or adjusted under 35 U.S.C. 154(b) by 2477 days.

(21) Appl. No.: 11/122,758

(22) Filed: May 5, 2005

(65) Prior Publication Data

US 2005/0261700 A1 Nov. 24, 2005

Related U.S. Application Data

(60) Provisional application No. 60/579,388, filed on Jun. 14, 2004.

(30) Foreign Application Priority Data

May 5, 2004 (EP) .................................... 04010669

(51) Int. Cl.
*A61B 17/72* (2006.01)
(52) U.S. Cl. ......................................... 606/62; 606/329
(58) Field of Classification Search ................... 606/62, 606/329, 130
See application file for complete search history.

(56) References Cited

U.S. PATENT DOCUMENTS

| | | | |
|---|---|---|---|
| 5,015,842 A * | 5/1991 | Fradenburgh et al. | ... 250/227.15 |
| 5,411,503 A | 5/1995 | Hollstien et al. | |
| 5,417,688 A | 5/1995 | Elstrom et al. | |
| 5,540,691 A * | 7/1996 | Elstrom et al. | .................. 606/64 |
| 5,584,838 A | 12/1996 | Rona et al. | |
| 6,005,955 A * | 12/1999 | Kroll et al. | ..................... 381/328 |
| 2003/0055435 A1* | 3/2003 | Barrick | ......................... 606/102 |
| 2003/0114846 A1* | 6/2003 | Fuimaono et al. | .............. 606/41 |
| 2003/0181918 A1* | 9/2003 | Smothers et al. | ............... 606/86 |

FOREIGN PATENT DOCUMENTS

| | | | |
|---|---|---|---|
| JP | 2001-330415 A | * | 11/2001 |
| WO | 03/068090 A1 | | 8/2003 |
| WO | 2004/034914 A2 | | 4/2004 |

OTHER PUBLICATIONS

European Search Report for corresponding Application No. 04010669.2 dated Oct. 12, 2004.

* cited by examiner

*Primary Examiner* — Eduardo C Robert
*Assistant Examiner* — Julianna N Harvey
(74) *Attorney, Agent, or Firm* — Renner, Otto, Boisselle & Sklar, LLP

(57) ABSTRACT

A tracking device for an intramedullary pin whose spatial position is determined and/or tracked in image-guided surgery, including a reference device at a proximal end of the intramedullary pin and a medical navigation system which locates the reference device and determines the orientation of the intramedullary pin from the proximal end. A deformation detection device detects deformations of the intramedullary pin and communicates the deformations to the navigation system. Also provided is a tracking method for determining or tracking the spatial position of an intramedullary pin in image-guided surgery, and to an intramedullary pin that includes a deformation detection device.

3 Claims, 2 Drawing Sheets

INTRAMEDULLARY PIN TRACKING

RELATED APPLICATION DATA

This application claims priority of U.S. Provisional Application No. 60/579,388 filed Jun. 14, 2004, which is hereby incorporated herein by reference in its entirety.

FIELD OF THE INVENTION

The present invention relates to the field of intramedullary pin tracking and, more particularly, to a method, apparatus and system for tracking an intramedullary pin and ascertaining a deformation of the pin as it is inserted into an object, such as a bone.

BACKGROUND OF THE INVENTION

The use of intramedullary pins is a known and established form of treatment for fractures in long bones. Intramedullary pins include fixing holes or bores at the proximal and distal ends of the intramedullary pin (the implant), and screws can be inserted into the fixing holes or bores in order to fix or attach the intramedullary pin to the fractured bone.

One problem with conventional intramedullary pins is that the implanted intramedullary pin is deformed by the shape of the long bone as the intramedullary pin is introduced into the bone. Due to this deformation, the position and orientation of the distal end of the intramedullary pin is in principle unknown and, therefore, the position and orientation of the distal fixing bore also is unknown.

In order to insert the fixing screws into the distal fixing bore, the position of the distal fixing bore must be determined, and this is conventionally achieved with the aid of x-ray images. Surgeons generally use a C-arc fluoroscopy apparatus to determine the position of the pin and/or bore, thus facilitating the insertion of the screw into the distal fixing bore.

A disadvantage of this conventional approach is that it exposes the patient and operating team to an undesirable radiation load. A further disadvantage in using C-arcs is the lack of a third dimension. On the basis of intra-operatively produced x-ray projections, even from a number of angles, a sufficient spatial orientation for reliably controlling the introduction of screws in all three dimensions and all degrees of freedom generally is lacking.

In order to solve these problems, an attempt has been made to use an optical target system such as that described in U.S. Pat. No. 5,417,688, wherein a light source is attached to the distal end of the intramedullary pin, and the light source is used to determine the orientation of the distal fixing bore. The intent is to use the light radiation transmitted onto the surface of the patient's body to orient a drill. The light source, however, can be difficult to identify, resulting in inaccurate identification of the fixing bore location.

Alternatively, a suggestion also has been made to use magnetic targeting systems such as, for example, those described in U.S. Pat. Nos. 6,162,228, 5,411,503 and 5,584,838, in which a special configuration of magnets is arranged or a predetermined magnetic field is generated at the distal end of the intramedullary pin. The magnetic field then is used to determine the orientation of the distal fixing bore. The surgeon uses a navigation tool provided with a magnetic sensor system in order to fix the intramedullary pin. A drawback to these systems is that they can be costly and relatively susceptible to faults. The latter particularly applies if steel pins are used.

Another common approach is based on using existing navigation methods that provide for tracking a pin, and integrating C-arc into navigation. In these systems, experience has shown that solely tracking the pin, without taking into account the deformation, generally leads to incorrect bores, despite the use of fluoroscopy in combination with navigation.

Another disadvantage of these known methods is that they are based on the use of radiation (C-arc) for imaging, and the position of the through-bores in the image is determined manually and imprecisely (due to misinterpretation of the displayed projection, for example). In order to be able to navigate in the C-arc images, the images must be provided in a calibrated form (rectified and with the spatial position of the projection known when recording) and the bone structure in which the intramedullary pin is situated must be provided with a reference array (additional invasiveness).

SUMMARY OF THE INVENTION

The present invention provides a method, apparatus and system that detects and compensates for deformation in the intramedullary pin as it is inserted into the bone. More particularly, the present invention detects the deformation in the intramedullary pin and provides the information to a medical navigation system or the like. The deformation can be detected by a deformation detection device that extends along the intramedullary pin, wherein the deformation detection device communicates the deformation to the navigation system. An advantage of the present invention is that it provides precise navigation, while minimizing the invasive experience of the patient.

In practice, information on the position of the distal end of the intramedullary pin is composed of two pieces of information; an absolute position of the proximal end (via a reference device) of the intramedullary pin and information on the deformation, i.e., information relative to the non-deformed pin. The present invention enables one to deviate from the principle that previously had been used in both optical and magnetic target finding methods, namely that of directly and absolutely determining the position and orientation of the distal end of the intramedullary pin or bore. Faults and imprecision, which can occur when making such direct determinations due to patient tissue around the outside of the intramedullary pin, can be overcome by the present invention. Further, determining the target trajectory of the through-bore in the intramedullary pin can be controlled without using radiation in any of the degrees of freedom (three dimensions), thereby reducing the radiation load to the patient and operating team. Additionally, in accordance with the present invention, reference clamps are not required, thereby reducing the time and effort typically required to arrange such clamps. Further, this results in a less invasive experience for the patient.

In accordance with a preferred embodiment, the deformation detection device detects bending (both angular and torsional) in the intramedullary pin. In particular, the deformation detection device can extend from substantially the proximal end to substantially the distal end of the intramedullary pin, preferably from the proximal to the distal determining means, in particular the fixing bore of the pin.

The deformation detection device can be advantageously situated in the interior of the intramedullary pin and can be a fiber optic structure, in particular a glass fiber optic structure, which detects deformations on the basis of differences in light transit times. The fiber optic structure can include a structure with sequentially arranged fiber optic loops. Alternatively or additionally, the fiber optic structure can include at least two loop structures orientated at an angle with respect to each other, in particular perpendicular to each other, in order to facilitate the determination of torsional bending.

In a tracking method in accordance with the invention for determining or tracking the spatial position of an intramedullary pin in image-guided surgery, a reference device can be arranged on the proximal end of the intramedullary pin and located using a medical navigation system. The orientation of the intramedullary pin from the proximal end then can be determined, wherein deformations of the intramedullary pin can be detected by the deformation detection device extending along the intramedullary pin and communicated to the navigation system. Using this information, the position of the intramedullary pin after deformation can be displayed in the navigation system and, with the aid of this information, detected bending (both angular and torsional) in the intramedullary pin can be used when calculating the orientation of the fixing bore at the distal end, thereby enabling a fixing screw to be precisely inserted into the fixing bore.

A number of different technologies are combined by the present invention, including:

1. virtually navigating an inelastic device with the aid of image-guided surgery (optical tracking system);
2. virtually detecting deformations, wherein deformations are detected, calculated and visualized;
3. using intramedullary pins; and
4. using target systems for fixing intramedullary pins.

In virtual navigation (1), the geometry of the pin (and therefore the position of the transit trajectory of the fixing screw) can be stored in a database, in order to provide enough information to describe in full a spatial change in position of the transit trajectory using the deformation of the intramedullary pin. Alternatively, the invention can be employed without a database. The trajectory can then be determined ("calibrated") before inserting the pin (non-deformed) and can be made known to the navigation system, e.g., the transit trajectory of the bore can be registered to the reference structure. Thus, for example, a pointer, a drill or a screw having an independent reference array can be guided through the bore of the intramedullary pin. The intramedullary pin, together with its reference array, can be arranged within a camera system of the navigation system, thereby communicating the trajectory orientation of the non-deformed pin to the navigation software.

The target systems mentioned last (4) can process the information available to the navigation system once the position has been detected in accordance with the invention.

In the following, the invention is explained in more detail on the basis of an exemplary embodiment.

DETAILED DESCRIPTION

Figure 1:
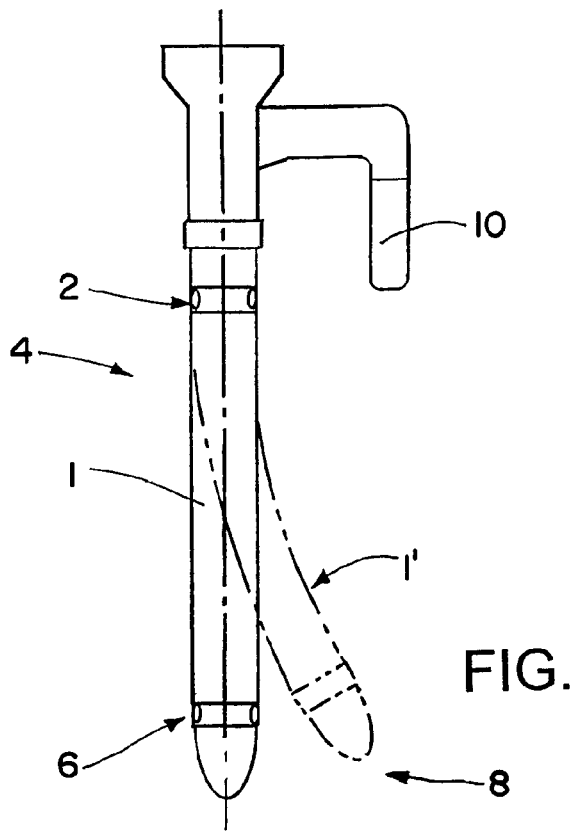
FIG. 1 is a schematic representation of an intramedullary pin comprising a positioning aid attachment.

FIG. 1 illustrates the intramedullary pin 1 in its non-deformed shape and (by a broken line) a deformed intramedullary pin 1'. The intramedullary pin 1 can include an elongated shaft having a fixing bore 2 at its proximal end 4 and a fixing bore 6 at its distal end 8. Furthermore, the intramedullary pin 1 shown in FIG. 1 is attached to a positioning aid attachment 10, which facilitates insertion of the intramedullary pin into a bone 12.

Figure 2:
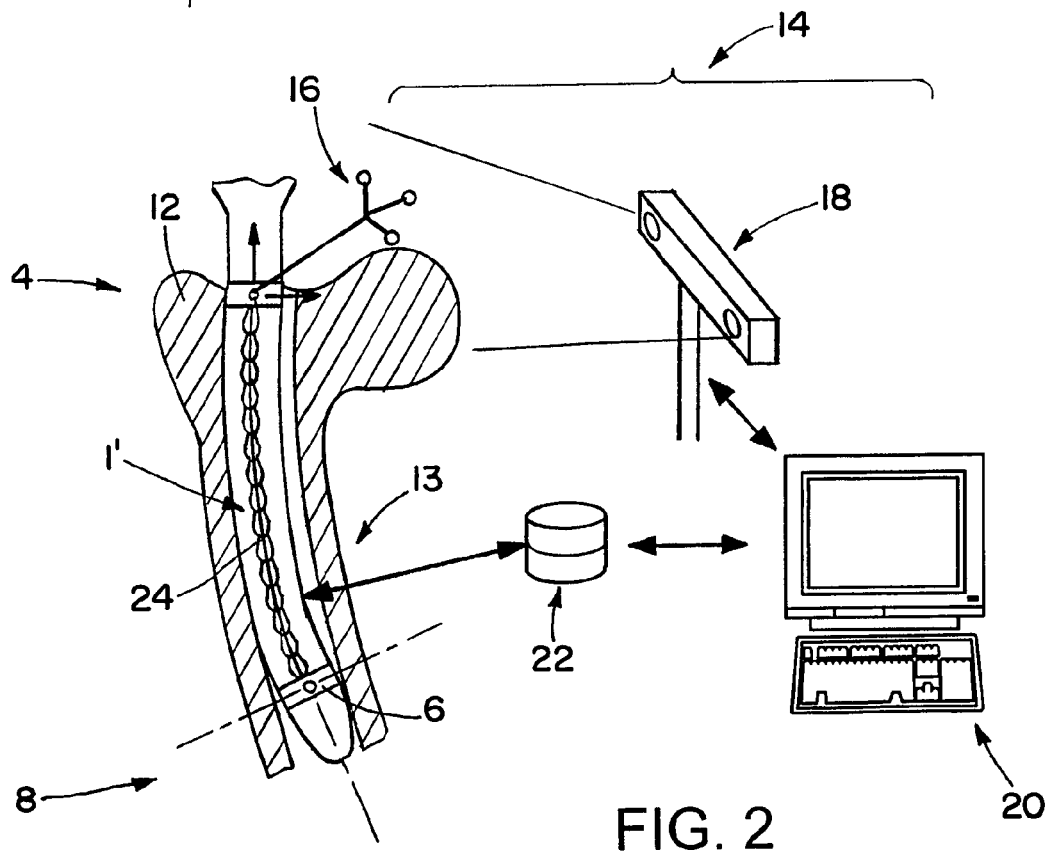
FIG. 2 illustrates a deformed intramedullary pin, inserted into a bone, and a tracking system in accordance with the invention.

The pin 1', inserted in a bone and thus deformed, is shown in FIG. 2. The bone 12 includes a bend 13, which the intramedullary pin follows when it is inserted into the bone. As a result of the bend 13, the fixing bore 6 comes to rest obliquely at the distal end 8. In order to determine the position and orientation of the fixing bore 6 and, therefore, to be able to precisely insert a fixing screw into the fixing bore 6, a tracking system 14 in accordance with the invention is employed. The tracking system 14 includes a reference structure 16, such as, for example, a three-armed reference array or reference star including passive (e.g., reflective) markers located at the proximal end 4 of the intramedullary pin, where the pin 1' protrudes out of the bone 12. The reference array 16 can be located by a navigation system, which is shown schematically and includes a camera array 18 and computer 20 with a screen output. The computer 20 also includes a database 22 in which the information on the original shape of the intramedullary pin 1 is stored. With the aid of the navigation system (e.g., the camera array 18, computer 20 and database 22), which can locate the reference array 16, the position of the intramedullary pin 1 at the proximal end 4 can be ascertained, as well as the direction in which the intramedullary pin would extend if it were not deformed.

In order to detect the deformation of the intramedullary pin (e.g., the angular and/or torsional bending of the intramedullary pin) and to superimpose the deformation on the data originating from the reference array 16 so as to ascertain the position and orientation of the bore 6, a deformation detection device 24 is arranged inside the intramedullary pin 1. The deformation detection device includes various glass fiber strips or loops, the arrangement of which is shown in FIGS. 3 and 4.

Figure 3:
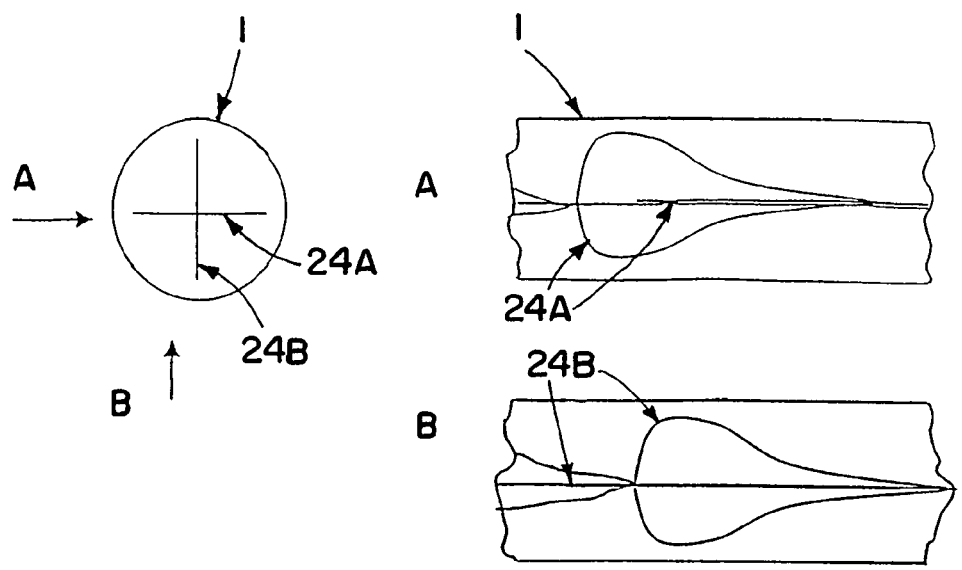
FIGS. 3 and 4 illustrate arrangements of fiber optic structures in an intramedullary pin.

FIG. 3 illustrates a cross-section through the intramedullary pin 1, from which it may be seen that two optical fiber structures 24A, 24B are arranged therein, perpendicular to each other. The views A and B, which are indicated on the left of the cross-section, are shown again to the right of the cross-section. The loop shape of the glass optical fiber strips 24A and 24B can likewise be seen. The perpendicularly arranged optical fiber strips or loops 24A and 24B are offset axially with respect to each other. The knowledge of the position of the trajectory relative to the reference array 16, when deformed, is stored in the database 22 (and/or is made known to the system beforehand by calibrating). By superimposing the deformation and the tracking information, the altered position of said trajectory is obtained.

Figure 4:
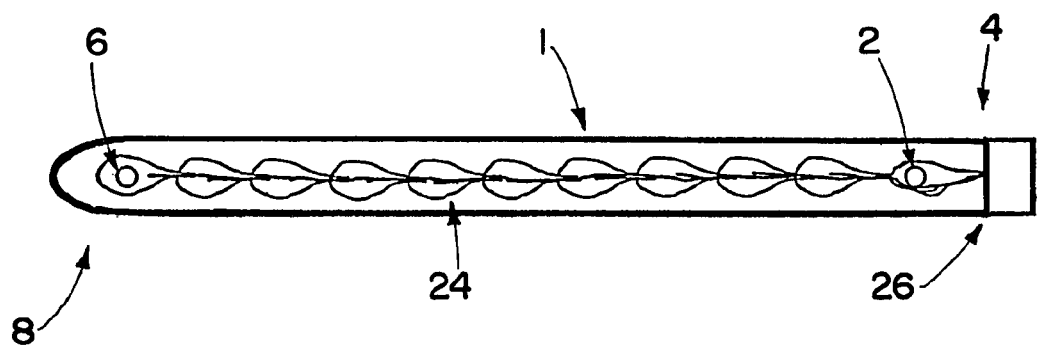

FIG. 4 also shows that the loops of the glass fibre array extend from the proximal fixing hole 2 to the distal fixing hole 6 in the intramedullary pin 1, in order that the entire area of interest can be detected regarding its deformation. An interface 26, such as a digital communication link or the like, for transmitting the deformation data to the navigation system is also shown schematically in FIG. 4, at the proximal end 4 of the intramedullary pin 1. The deformation data can be transmitted by a wired or wireless communication link.

In the event of deformation, each glass fiber experiences an individual change in transit time for its light beam, and the deformation can be calculated on the basis of the resultant delay. The integrated glass fiber sensor will thus be able to send a deformation feedback for the intramedullary pin 1 to the navigation system in real time. The navigation system in turn displays the intramedullary pin in its actual state, e.g., showing actual deformations of the pin, relative to an already registered part of the patient's body (bone), in real time. With the aid of this visualization, the distal fixing screw can be precisely introduced into the fixing bore 6.

What is claimed is:

1. A tracking system for an intramedullary pin whose spatial position is determined and/or tracked in image-guided surgery, said intramedullary pin having a proximal end and a distal end, comprising:
    a reference device configured for attachment to the proximal end of said intramedullary pin;
    a medical navigation system configured to locate said reference device and to determine an orientation of said intramedullary pin from the proximal end based on the location of the reference device; and
    a deformation detection device configured to detect deformations of said intramedullary pin and communicate the deformations to said navigation system, wherein said intramedullary pin includes an interior cavity, and said deformation detection device extends in the interior cavity of said intramedullary pin.

2. A tracking system for an intramedullary pin whose spatial position is determined and/or tracked in image-guided surgery, said intramedullary pin having a proximal end and a distal end, comprising:
    a reference device configured for attachment to the proximal end of said intramedullary pin;
    a medical navigation system configured to locate said reference device and to determine an orientation of said intramedullary pin from the proximal end based on the location of the reference device; and
    a deformation detection device configured to detect deformations of said intramedullary pin and communicate the deformations to said navigation system, wherein said deformation detection device is a fiber optic structure that detects deformations on the basis of differences in light transmit times, and wherein said fiber optic structure comprises a structure with sequentially arranged fiber optic loops.

3. A tracking system for an intramedullary pin whose spatial position is determined and/or tracked in image-guided surgery, said intramedullary pin having a proximal end and a distal end, comprising:
    a reference device configured for attachment to the proximal end of said intramedullary pin;
    a medical navigation system configured to locate said reference device and to determine an orientation of said intramedullary pin from the proximal end based on the location of the reference device; and
    a deformation detection device configured to detect deformations of said intramedullary pin and communicate the deformations to said navigation system, wherein said deformation detection device is a fiber optic structure that detects deformations on the basis of differences in light transmit times, and wherein said fiber optic structure comprises at least two loop structures orientated substantially perpendicular to each other.

* * * * *